United States Patent [19]

Stuetz

[11] Patent Number: 4,684,661

[45] Date of Patent: Aug. 4, 1987

[54] ANTI-FUNGAL HOMOPROPARGYLAMINES, COMPOSITIONS, AND METHOD OF USE THEREFOR

[75] Inventor: Anton Stuetz, Maria-Enzersdorf, Austria

[73] Assignee: Sandoz Ltd., Basel, Switzerland

[21] Appl. No.: 799,807

[22] Filed: Nov. 20, 1985

[30] Foreign Application Priority Data

Nov. 22, 1984 [DE] Fed. Rep. of Germany ....... 3442529
Aug. 10, 1985 [DE] Fed. Rep. of Germany ....... 3528736

[51] Int. Cl.⁴ .................... A61K 31/34; A61K 31/38; A61K 31/40; A61K 31/445; C07D 403/04; C07D 405/04; C07D 409/04
[52] U.S. Cl. .................................. 514/443; 514/212; 514/277; 514/337; 514/339; 514/357; 514/408; 514/414; 514/415; 514/422; 514/428; 514/432; 514/456; 514/467; 514/470; 514/653; 514/657; 540/596; 546/273; 546/274; 546/283; 546/333; 548/468; 548/550; 564/355; 564/366; 564/387; 549/23; 549/49; 549/58; 549/407; 549/467
[58] Field of Search .................... 549/23, 49, 58, 407, 549/467; 514/432, 443, 456, 467, 470; 540/596; 546/273, 274, 283, 333; 548/468, 550; 514/212, 277, 337, 339, 357, 408, 414, 415, 422, 428

[56] References Cited

U.S. PATENT DOCUMENTS

| 4,066,648 | 1/1978 | Oka et al. | 549/407 |
| 4,282,251 | 8/1981 | Berney | 564/275 |
| 4,309,439 | 1/1982 | Ohno et al. | 549/58 |

FOREIGN PATENT DOCUMENTS

| 0024587 | 3/1981 | European Pat. Off. | 549/23 |
| 2116171 | 9/1983 | Switzerland | 549/23 |

Primary Examiner—Henry R. Jiles
Assistant Examiner—J. G. Mullins
Attorney, Agent, or Firm—Gerald D. Sharkin; Richard E. Vila

[57] ABSTRACT

The invention relates to novel homopropargylamines of formula I

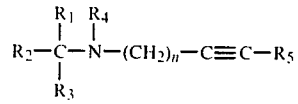

wherein
n is 2 or 3,
$R_1$ is a group of formula IIa, IIb or IIc

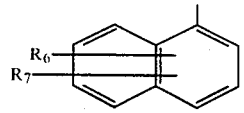

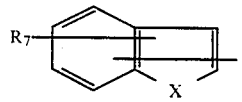

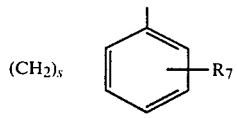

in which
$R_6$ and $R_7$ independently are H, halogen, $CF_3$, lower alkyl or lower alkoxy,
s is a number of 3 to 5,
X is O, S, $OCH_2$, $SCH_2$, $CH_2$ or $NR_8$, and
$R_8$ is H or lower alkyl,
$R_2$ is H or lower alkyl, either
$R_3$ and $R_4$, independently, are H or lower alkyl, or
$R_3$ and $R_4$ together are $(CH_2)_u$, in which u is a number of 3 to 5, and
$R_5$ is H, alkenyl or is a group selected from alkyl, trialkylsilyl, dialkylphenylsilyl, phenyl, phenylalkyl and cycloalkyl, in which alkyl, phenyl and cycloalkyl groups or moieties are unsubstituted or substituted by OH, lower alkyl, lower alkoxy, phenyl or halogen, in free base form or acid addition salt form thereof, their preparation, their chemotherapeutical and agricultural use and to compositions comprising such novel compounds and suitable for such use.

15 Claims, No Drawings

ANTI-FUNGAL HOMOPROPARGYLAMINES, COMPOSITIONS, AND METHOD OF USE THEREFOR

The invention relates to novel homopropargylamines of formula I

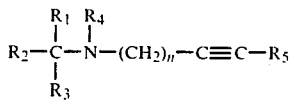

wherein
n is 2 or 3,
$R_1$ is a group of formula IIa, IIb or IIc

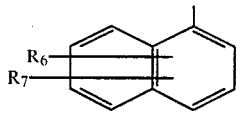

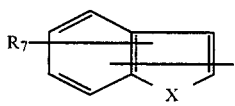

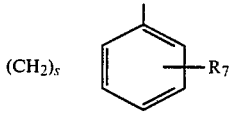

in which
$R_6$ and $R_7$ independently are H, halogen, $CF_3$, lower alkyl or lower alkoxy,
s is a number of 3 to 5,
X is O, S, $OCH_2$, $SCH_2$, $CH_2$ or $NR_8$, and
$R_8$ is H or lower alkyl,
$R_2$ is H or lower alkyl, either
$R_3$ and $R_4$, independently, are H or lower alkyl, or
$R_3$ and $R_4$ together are $(CH_2)_u$, in which u is a number of 3 to 5, and
$R_5$ is H, alkenyl or is a group selected from alkyl, trialkylsilyl, dialkylphenylsilyl, phenyl, phenylalkyl and cycloalkyl, in which alkyl, phenyl and cycloalkyl groups or moieties are unsubstituted or substituted by OH, lower alkyl, lower alkoxy, phenyl or halogen,
in free base form or acid addition salt form thereof.

The invention also provides processes for the production of compounds of formula I, comprising (a) reacting a compound of formula III

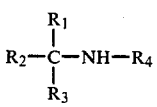

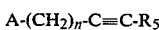

wherein $R_1$, $R_2$, $R_3$ and $R_4$ are as defined above, with a compound of formula IV $$A\text{-}(CH_2)_n\text{-}C\equiv C\text{-}R_5 \qquad IV$$

wherein $R_5$ and n are as defined above, and A is a leaving group, which is split off under the reaction conditions, (b) obtaining compounds of formula Ia

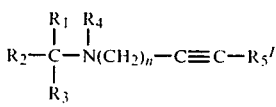

wherein $R_1$, $R_2$, $R_3$, $R_4$ and n are as defined above, and $R_5{}'$ is dialkylphenylsilyl, trialkylsilyl or α-hydroxyalkyl, by reacting a compound of formula V

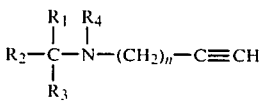

wherein $R_1$, $R_2$, $R_3$, $R_4$ and n are as defined above, in metal form, with the corresponding dialkylphenylsilylhalogen, trialkylsilylhalogen or oxoalkane compound, or (c) dehydrating compounds of formula Ia wherein $R_5{}'$ is α-hydroxyalkyl to the corresponding compounds of formula I wherein $R_5$ is 1-alken-1-yl, and whereby, where desired functional groups may be protected during the reaction by protecting groups, which are split off after completion of the reaction.

The compounds of formula I are obtained in free base form or in acid addition salt form; free base forms of compounds of formula I may be converted into corresponding acid addition salts in conventional manner and vice versa.

Process (a) may for example be carried out in a solvent which is inert under the reaction conditions, such as lower alcohol, e.g. ethanol, optionally in admixture with water, an aromatic hydrocarbon e.g. benzene, toluene, a cyclic ether e.g. dioxane, a carboxylic acid N,N-dialkylamide e.g. dimethylformamide. The reaction temperature is conveniently between room temperature and boiling temperature of the reaction mixture. The reaction is conveniently effected in the presence of an acid binding agent, such as an alkalimetalcarbonate, e.g. $Na_2CO_3$.

Process (b) may for example be carried out in a solvent which is inert under the reaction conditions such as a cyclic ether, e.g. tetrahydrofurane, under exclusion of water, preferably at low temperature.

The dehydration according to process (c) may be carried out in a manner known per se, for example with p-toluenesulphonic acid or by treatment with mesylchloride, in the presence of a base such as triethylamine, in a solvent which is inert under the reaction conditions, e.g. $CH_2Cl_2$.

The compounds of formula I may contain one or more chiral centres and/or double bonds. They are, in general, obtained in the form of racemic, diastereomeric and/or cis/trans mixtures. However, such mixtures can, if desired, be separated either completely or partly into the individual compounds or desired isomer mixtures by methods known in the art.

Alkyl groups may be straight or branched. They may contain 1 to 12, preferably 1 to 8, particularly 1 to 5 carbon atoms.

Lower alkyl and lower alkoxy substituents have preferably 1 to 4, more preferably 1 or 2 carbon atoms.

Suitable halogen substituents of compounds of formula I are e.g. F, Cl and Br.

Where $R_5$ is alkenyl it comprises preferably 3 to 6, particularly 3 or 4 carbon atoms, and stands for example for allyl or propenyl.

Where $R_5$ is cycloalkyl, it comprises preferably 3 to 6 carbon atoms.

Where $R_5$ is phenylalkyl, it is preferably phenyl-$C_1$-$_5$alkyl.

Where $R_5$ is alkyl, alkenyl or phenyl alkyl, it is preferably branched in α-position of the acetylenic bond; particularly preferred alkyl and phenylalkyl significances of $R_5$ are tert. alkyl and phenyl substituted derivatives thereof, whereby these groups may be unsubstituted or substituted as stated hereinabove.

In compounds of formula IV, A signifies for example halogen, particularly Cl or Br, or an organic sulfonyloxy group having 1 to 10 carbon atoms, for example alkylsulfonyloxy, (particularly with 1 to 4 carbon atoms) such as methylsulfonyloxy, or alkylphenylsulfonyloxy (e.g. with 7 to 10 carbon atoms) such as tosyloxy.

The starting materials are either known, or may be obtained in a manner known per se or analogous to methods disclosed herein.

The compounds of formula I exhibit chemotherapeutic activity. In particular, they exhibit antimycotic activity, as indicated in vitro in various families and types of mycetes, including Trichophyton spp., Aspergillus spp., Microsporum spp., *Sporotrix schenkii* and Candida spp., at concentrations of, for example 0.003 to 50 μg/ml, and in vivo in the experimental skin mycosis model in guinea pigs. In the latter test, the test substance is administered daily for 7 days beginning 24 hours after the infectionon local application by rubbing the test substance (taken up in polyethylene glycol) on the skin surface. In addition the Candida activity may be shown in vivo employing conventional intra-vaginal/intrauterine- or disseminated-infection models on mice or rats. The activity is shown on local application at concentrations of for example 0.01 to 0.2%. The oral activity is shown in vivo in the guinea-pig-trichophytosis at dosages of, for example, 2 to 70 mg/kg.

The compounds are therefore indicated for use as antimycotic agents.

The compounds may be used in free base form or in the form of chemotherapeutically acceptable acid addition salts. Such salt forms exhibit the same order of activity as the free base forms. Suitable such salts forms are e.g. hydrochloride, hydrogen fumarate or naphtha-line-1,5-disulphonate. The compounds may be employed in a manner analogous to that known for compounds having the same chemotherapeutical use, such as griseofulvine, and may be administered parenterally, topically, intravenously or topically.

The invention therefore also concerns a method of treating diseases or infections caused by mycetes which comprises administering to a subject in need of such treatment an effective amount of a compound of formula I or a chemotherapeutically acceptable acid addition salt thereof. It also relates to compounds of formula I or chemotherapeutically acceptable acid addition salts thereof for use as chemotherapeutic agents especially as anti-mycotics.

The compounds may be admixed with conventional chemotherapeutically acceptable diluents and carriers, and, optionally, other excipients and administered e.g. orally in such forms as tablets or capsules. The compounds may alternatively be administered topically (in such conventional forms as ointments or creams), parenterally or intravenously. The amount or concentration of the active substance will, or course, vary depending on the compound employed, the treatment desired and the nature of the form etc. In general, however, satisfactory results are obtained e.g. in topical application forms at concentrations of from 0.05 to 5, in particularly 0.1 to wt.%.

For oral use a suitable total daily dosage is from about 70 to 2000 mg and dosage forms suitably given two to four times daily at dosages of about 17.5 to 1000 mg or in retard form.

The compounds of formula I in free base form or in agriculturally acceptable acid addition salt form (hereinafter agrichemicals of the invention) are useful for combatting phytopathogenic fungi. The interesting fungicidal activity is i.a. observed in in vivo tests against rusts, such as Uromyces appendiculatus on runner beans and Puccinia on wheat, and powdery mildews, such as *Erysiphe cichoracearum* cuccumber, *E. Graminis* on wheat, *Podosphaera leveotricha* on apple and *Uncinula necator* on grapevine at test concentrations of from 0.5 to 500 ppm. The test results also indicate a good plant tolerance.

The agrichemicals of the invention are therefore indicated for use in combatting phytopathogenic fungi, e.g. Basidiomycetes of the order Uredinales such as Puccinia spp., Hemileia spp., Uromyces spp. and Ascomycetes of the order Erysiphales, such as Erysiphe spp., Podosphaera spp. and Uncinula spp.

The amount of agrichemicals of the invention to be applied, will depend on various factors such as the compound employed, the subject of the treatment (plant, soil, seed), the type of treatment (e.g. spraying, dusting, dressing), the purpose of the treatment (prophalactic or therapeutic), the type of fungi to be treated and the application time.

In general, satisfactory results are obtained, if the agrichemicals of the invention are applied in an amount of from about 0.005 to 2.0, preferably about 0.01 to 1 kg/ha, in the case of a plant or soil treatment; e.g. 0.04 to 0.125 kg of active ingredient (a.i.) per ha in crops such as cereals, or concentrations of 1 to 5 g of a.i. per hl in crops such as fruits, vineyards and vegetables (at an application volume of from 300 to 1000/ha-depending on the size or leaf volume of the crop-which is equivalent to an application rate of approximately 10–50 g/ha). The treatment can, if desired, be repeated, e.g. at intervals of 8 to 30 days.

Where the agrichemicals of the invention are used for seed treatment, satisfactory results are in general obtained, if the compounds are used in an amount of from about 0.05 to 0.5, preferably about 0.1 to 0.3 g/kg seeds.

The agrichemicals of the invention in agriculturally acceptable salt form exhibit in general, the same order of activity as the corresponding compounds in free base form.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, peanuts, cotton, flax, maize (corn), vineyards, fruits (e.g. apples, pears, prunes, bananas) and in cereals (e.g. wheat, oats, barley, rice).

The invention therefore provides a method of combatting phytopathogenic fungi, comprising applying to the fungi or their locus a fungicidally effective amount of a compound of formula I in free base form or in agriculturally acceptable acid addition salt form.

The invention also provides fungicidal compositions comprising as fungicide a compound of formula I in free base form or in agriculturally acceptable acid addition salt form in association with agriculturally acceptable diluent (hereinafter diluent) and, optionally, additional excipients such as surfactants. In general, such compositions comprise 0.0005 to 90, e.g. 0.001 to 70 percent by weight of active ingredient.

The term diluents as used herein means liquid or solid, agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Such formulations, especially these used in spray form, such as water dispersible concentrates or wettable powders, may contain surfactants (e.g. up to 20% by weight) such as wetting and dispersing agents, e.g. the condensationproduct of formaldehyde with naphthalene sulphonate, an alkylarylsulphonate, in lignin sulphonate, a fatty alkyl sulphate, an ethoxylated alkylphenol and an ethoxylated faty alcohol.

In addition to the usual diluents and surfactants, the compositions of the invention may comprise further additives with special purposes, e.g. stabilizers, desactivators (for solid formulations or carriers with an active surfact), agents for improving the adhesion to plants, corrosion inhibitors, anti-foaming agents and colorants. Moreover, further fungicides with similar or complementary fungicidal activity, e.g. sulphur, chlorothalonil, dithiocarbamates such as mancozeb, maneb, zineb, propineb, trichloromethane-sulphenylphthalimides and analoges such as captan, captafol and folpet, benzimidazoles such as benomyl and carbendazim, or other beneficially-acting materials, such as insecticides may be present in the formulations.

Examples of plant fungicide formulations are as follows:

a. Wettable Powder Formulation

10 Parts of a compound of formula I are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor.

b. Granules

Onto 94.5 parts by weight of quartz sand in a tumbler mixer are sprayed 0.5 parts by weight of a binder (non-ionic tenside) and the whole thoroughly mixed. 5 Parts by weight of a compound of formula I are then added and thorough mixing continued to obtain a granulate formulation with a particle size in the range of from 0.3 to 0.7 mm.

c. Emulsion Concentrate

25 Parts be weight of a compound of formula I are mixed with 10 parts by weight of an emulsifier and 65 parts by weight of xylene. The concentrate is siluted with water to the desired concentration.

d. Seed Dressing

45 Parts of a compound of the invention are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherance and may be applied to seeds, e.g. by mixing for 2 to 5 minutes in a slowly turning vessel.

In preferred compounds of formula I, the substituents have one or more of the following significances:

$R_1$ is IIa or IIb
X is O or S
$R_6$ is hydrogen
$R_7$ is H, halogen (particularly Cl or Br) or $C_{1-4}$alkyl (particularly $CH_3$)
$R_2$ is H or $C_{1-4}$alkyl
$R_3$ is H or together with $R_4$ $(CH_2)_4$
$R_4$ is $C_{1-4}$alkyl
$R_5$ is H, $C_{1-8}$alkyl (particularly $C_{1-5}$alkyl), $C_{3-6}$cycloalkyl, $C_{3-5}$alkenyl, $C_{1-4}$alkoxy-$C_{1-5}$alkyl, phenyl-$C_{1-5}$alkyl, halogenphenyl-$C_{1-5}$alkyl, hydroxy-$C_{1-5}$alkyl, tri($C_{1-5}$alkyl)silyl, di($C_{1-5}$alkyl)phenylsilyl.

In the particularly preferred compounds of formula I the substituents have one or more of the following significances:

$R_1$ is a 1-naphthyl, a benzofuranyl or a benzo[b]thienyl group, which group is unsubstituted or monosubstituted by halogen (especially Cl or Br) or $C_{1-4}$alkyl (especially $CH_3$)
$R_2$ and $R_3$ are H
$R_4$ is $CH_3$ or $C_2H_5$, particularly $CH_3$
$R_5$ is H, $C_{3-6}$cycloalkyl or a tertiary group selected from $C_{4-5}$alkyl, $C_{1-4}$alkoxy-$C_{3-5}$alkyl, halogenphenyl-$C_{3-5}$alkyl, phenyl-$C_{3-5}$alkyl or hydroxy-$C_{3-5}$alkyl which group is tied by its tert. carbon atom to the homopropargyl group.

The following examples illustrate the invention. Temperatures are in Centigrades.

EXAMPLE 1

N-Methyl-N-(1-naphthylmethyl)-5,5-dimethyl-3-hexynamine

To a solution of 540 mg 5,5-dimethyl-3-hexyn-1-ol in dimethylformamide (DMF) are added, at 0° 1.2 ml triethylamine. Then are added, dropwise, with stirring, 0.335 ml methanesulfonylchloride. After 2 hours of stirring at room temperature are added 740 mg N-methyl-1-naphthylmethylamine and the mixture is heated overnight at 80°. The solvent is evaporated in vacuum, the residue distributed between saturated aqueous $NaHCO_3$ solution and ethyl acetate, the organic phase washed, dried and evaporated. The crude residue is chromatographed over silicagel (with toluene/ethylacetate 9/1) and the title compound (Compound 1) obtained as an oil.

EXAMPLE 2

In a manner analogous to that described in Example 1 the following compounds of formula I are obtained:

| Cpd. | $R_1$ | $R_2$ | $R_3$ | $R_4$ | $R_5$ | n | Characterisation |
| --- | --- | --- | --- | --- | --- | --- | --- |

-continued

| | | | | | | | |
|---|---|---|---|---|---|---|---|
| 2 | 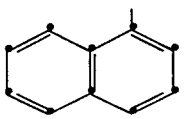 | H | H | CH$_3$ | $-\underset{\underset{CH_3}{\|}}{C}=CH_2$ | 2 | Oil |
| 3 | " | H | H | CH$_3$ | H | 2 | Oil |
| 4 | " | H | H | CH$_3$ | $-\underset{\underset{CH_3}{\|}}{\overset{\overset{CH_3}{\|}}{C}}-C_2H_5$ | 2 | Oil |
| 5 | " | H | H | CH$_3$ | $-\underset{\underset{CH_3}{\|}}{\overset{\overset{CH_3}{\|}}{C}}-C_6H_5$ | 2 | mp.(HCl): 106–110° |
| 6 | 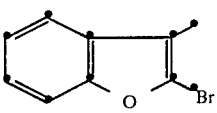 | H | H | CH$_3$ | —C(CH$_3$)$_3$ | 2 | Oil |
| 7 | 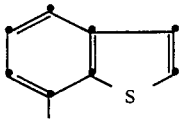 | H | H | CH$_3$ | " | 2 | mp. 35–37° |
| 8 | 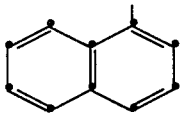 | H | —(CH$_2$)$_4$— | | " | 2 | mp. 82–84° |
| 9 | 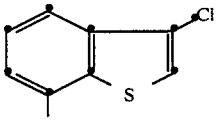 | H | H | CH$_3$ | —C(CH$_3$)$_3$ | 2 | mp: 62–64° |
| 10 | " | H | H | CH$_3$ | H | 2 | Oil |
| 11 | 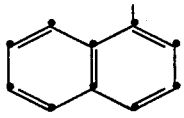 | H | H | CH$_3$ | C$_6$H$_5$ | 2 | Oil |
| 12 | " | H | H | CH$_3$ | $-\underset{\underset{CH_3}{\|}}{\overset{\overset{CH_3}{\|}}{C}}-OC_2H_5$ | 2 | Oil |
| 13 | 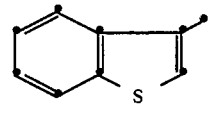 | H | H | CH$_3$ | —C(CH$_3$)$_3$ | 2 | Oil |
| 14 | 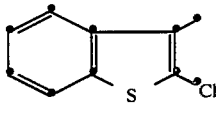 | H | H | CH$_3$ | " | 2 | Oil |
| 15 | 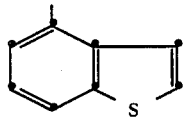 | H | H | CH$_3$ | " | 2 | mp.(HCl): 205–208° |

-continued

| # | Structure | | | | | | |
|---|---|---|---|---|---|---|---|
| 16 | benzothiophene-2-CH3 | H | H | CH3 | " | 2 | mp.(HCl): 185-190° |
| 17 | dihydronaphthalene | H | H | CH3 | " | 2 | Oil |
| 18 | naphthalene | H | H | CH3 | —C(CH3)2—C6H4—F | 2 | Oil |
| 19 | " | H | H | C2H5 | —C(CH3)3 | 2 | Oil |
| 20 | " | CH3 | H | CH3 | " | 2 | Oil |
| 21 | " | H | H | CH3 | cyclohexenyl | 2 | Oil |
| 22 | " | H | H | H | —C(CH3)3 | 2 | Oil |
| 23 | chromene | H | H | CH3 | —C(CH3)3 | 2 | Oil |
| 24 | naphthalene | H | H | CH3 | " | 3 | Oil |
| 25 | " | H | H | CH3 | —C(C2H5)2OH | 2 | Oil |
| 26 | " | H | H | CH3 | —C(CH3)2OH | 2 | Oil |
| 27 | " | H | H | CH3 | —Si(CH3)2C6H5 | 2 | Oil |
| 28 | " | H | H | CH3 | —Si(CH3)3 | 2 | Oil |
| 29 | " | H | H | CH3 | —C(C2H5)=CH—CH3 | 2 | Oil |

| Cpd. | SPEKTRA (CDCl3, TMS): |
|---|---|
| 1 | 8.2–8.4 (m, 1H); 7.65–7,95 (m, 2H); 7.25–7.6 (m, 4H); 3.93 (s, 2H); 2.25–2.8 (m, 4H); 2.24 (s, 3H); 1.18 (s, 9H). |
| 2 | 8.25–8.45 (m, 1H); 7.7–7.95 (m, 2H); 7.3–7.65 (m, 4H); 5.1–5.3 (m, 2H); 3.98 (s, 2H); 2.45–2.95 (m, 4H); 2.3 (s, 3H); 1.9 (m, 3H). |
| 3 | 8.2–8.4 (m, 1H); 7.6–7.9 (m, 2H); 7.2–7.6 (m, 4H); 3.9 (s, 2H); 2.2–2.9 (m, 4H); 2.26 (s, 3H); 2.0 (t, J = 2 Hz, 1H). |
| 4 | 8.2–8.4 (m, 1H); 7.7–7.95 (m, 2H); 7.25–7.6 (m, 4H); 3.95 (s, 2H); 2.3–2.8 (m, 4H); 2.25 (s, 3H); 1.4 (pseudogua, 2H); 1.14 (s, 6H), 0.95 (t, J = 7 Hz, 3H). |
| 5 | 8.25–8.4 (m, 1H); 7.7–7.95 (m, 2H); 7.2–7.65 (m, 9H); 3.97 (s, 2H); 2.4–2.9 (m, 4H); 2.28 (s, 3H); 1.55 (s, 6H). |
| 6 | 7.65–7.85 (m, 1H); 7.1–7.5 (m, 3H); 3.6 (s, 2H); 2.2–2.75 (m, 4H); 2.22 (s, 3H); 1.18 (s, 9H). |
| 7 | 7.65–7.85 (m, 1H); 7.2–7.5 (m, 4H); 3.8 (s, 2H); 2.3–2.8 (m, 4H); |

| | -continued |
|---|---|
| | 2.25 (s, 3H); 1.18 (s, 9H). |
| 8 | 8.4–8.7 (br, 1H); 7.25–7.95 (m, 6H); 3.7–4.0 (m, 1H); 3.2–3.4 (dbr, J = 11 Hz, 1H); 2.55–2.8 (m, 1H); 2.0–2.4 (m, 4H); 1.4–1.9 (m, 6H); 1.1 (s, 9H). |
| 9 | 7.78 (dd, J = 7μ, 2 Hz, 1H); 7.46 (d, J = 7 Hz, 1H); 7.3 (s, 1H); 7.3 (d, J = 7 Hz, 1H); 3.82 (s, 2H); 2.3–2.8 (m, 4H); 2.24 (s, 3H); 1.18 (s, 9H). |
| 10 | 7.78 (dd, J = 7μ, 2 Hz, 1H); 7.46 (d, J = 7 Hz, 1H); 7.3 (d, J = 7 Hz, 1H); 7.3 (s, 1H); 3.8 (s, 2H); 2.3–2.8 (m, 4H); 2.24 (s, 3H); 1.96 (t, J = 2 Hz, 1H). |
| 11 | 8.25–8.45 (m, 1H); 7.7–7.95 (m, 2H); 7.2–7.6 (m, 9H); 3.98 (s, 2H); 2.5–3.0 (m, 4H); 2.3 (s,3H). |
| 12 | 8.2–8.4 (m, 1H); 7.7–7.95 (m, 2H); 7.3–7.6 (m, 4H); 3.95 (s, 2H); 3.58 (qua, J = 7 Hz, 2H); 2.35–2.85 (m, 4H); 2.28 (s, 3H); 1.42 (s, 6H); 1.18 (t, J = 7 Hz, 3H). |
| 13 | 7.8–8.1 (m, 2H); 7.2–7.5 (m, 3H); 3.78 (s, 2H); 2.3–2.6 (m, 4H); 2.28 (s, 3H); 1.2 (s, 9H). |
| 14 | 7.8–8.1 (m, 1H); 7.6–7.8 (m, 1H); 7.2–7.5 (m, 2H); 3.76 (s, 2H); 2.3–2.8 (m, 4H); 2.22 (s, 3H); 1.2 (s, 9H). |
| 15 | 7.82 (m, 1H); 7.72 (dd, J = 5.5μ, 1 Hz, 1H); 7.45 (d, J = 5.5 Hz, 1H); 7.32 (d, J = 5.5 Hz, 1H); 7.3 (m, 1H); 3.84 (s, 2H); 2.3–2.8 (m, 4H); 2.22 (s, 3H); 1.2 (m, 9H). |
| 16 | 7.7–8.0 (m, 2H); 7.2–7.5 (m, 2H); 3.68 (s, 2H); 2.3–2.8 (m, 4H); 2.56 (s, 3H); 2.20 (s, 3H); 1.20 (s, 9H). |
| 17 | 6.95–7.2 (m, 3H); 3.55 (s, 2H); 2.7–2.95 (m, 4H); 2.3–2.7 (m, 4H); 2.22 (s, 3H); 1.8–2.0 (m, 4H); 1.20 (s, 9H). |
| 18 | 8.2–8.4 (m, 1H); 7.7–7.95 (m, 2H); 7.3–7.6 (m, 6H); 6.96 (t, J = 9 Hz, 2H); 3.96 (s, 2H); 2.4–2.9 (m, 4H); 2.28 (s, 3H); 1.52 (s, 6H). |
| 19 | 8.25–8.45 (m, 1H); 7.7–7.95 (m, 2H); 7.25–7.6 (m, 4H); 4.02 (s, 2H); 2.2–2.8 (m, 4+2H); 1.16 (s, 9H); 1.06 (t, J = 7 Hz, 3H). |
| 20 | 8.3–8.5 (m, 1H); 7.3–7.95 (m, 6H); 4.35 (qua, J = 7 Hz, 1H); 2.2–2.8 (m, 4H); 2.3 (s, 3H); 1.48 (d, J = 7 Hz, 3H); 1.18 (s, 9H). |
| 21 | 8.2–8.4 (m, 1H); 7.7–7.95 (m, 2H); 7.25–7.6 (m, 4H); 3.94 (s, 2H); 2.2–2.8 (m, 5H); 2.26 (s, 3H); 1.1–2.0 (m, 10H). |
| 22 | 8.1–8.3 (m, 1H); 7.7–8.0 (m, 2H); 7.2–7.65 (m, 4H); 4.25 (s, 2H); 2.2–3.0 (m, 4H); 1.8 (br, NH); 1.15 (s, 9H). |
| 23 | 6.7–7.4 (m, 4H); 5.78 (m, 1H); 4.8 (m, 2H); 3.30 (m, 2H); 2.3–2.8 (m, 4H); 2.26 (s, 3H); 1.2 (s, 9H). |
| 24 | 8.25–8.45 (m, 1H); 7.7–7.95 (m, 2H); 7.25–7.6 (m, 4H); 3.88 (s, 2H); 2.58 (t, J = 7 Hz, 2H); 2.18 (s, 3H); 2.16 (t, J = 7 Hz); 1.6–1.9 (m, 2H); 1.16 (s, 9H). |
| 25 | 8.2–8.4 (m, 1H); 7.7–7.95 (m, 2H); 7.25–7.65 (m, 4H); 3.94 (s, 2H); 2.35–2.85 (m, 4H); 2.28 (s, 3H); 1.8 (br, OH); 1.65 (qua, J = 7.5 Hz, 4H); 1.0 (t, J = 7.5 Hz, 6H). |
| 26 | 8.2–8.4 (m, 1H); 7.65–7.95 (m, 2H); 7.25–7.6 (m, 4H); 3.92 (s, 2H); 2.3–2.8 (m, 4H); 2.24 (s, 3H); 1.85 (br, OH); 1.44 (s, 6H). |
| 27 | 8.2–8.4 (m, 1H); 7.2–7.95 (m, 11H); 3.95 (s, 2H); 2.4–2.9 (m, 4H); 2.26 (s, 3H); 0.4 (s, 6H). |
| 28 | 8.2–8.4 (m, 1H); 7.7–8.0 (m, 2H); 7.3–7.65 (m, 4H); 3.90 (s, 2H); 2.25–2.8 (m, 4H); 2.25 (s, 3H); 0.2 (s, 9H). |
| 29 | 8.2–8.4 (m, 1H); 7.65–7.95 (m, 2H); 7.2–7.6 (m, 4H); 5.5–5.9 (m, 1H); 3.95 (s, 2H); 2.45–2.9 (m, 4H); 2.27 (s, 3H); 2.1 (quam, J = 7 Hz, 2H); 1.8 (m, 3H); 1.04 (t, J = 7 Hz, 3H). |

EXAMPLE 3

N-Methyl-N-(1-naphthylmethyl)-5-ethyl-5-hydroxy-3-heptyn-amine

To 2 g N-methyl-N-(1-naphthylmethyl)-3-butynamine in abs. tetrahydrofurane (THF) are added dropwise, at −70°, 5.6 ml of a 15% by weight solution of n-butyllithium in hexane and half an hour later, at −70°, 0.95 ml diethylketone. The mixture is stirred for 3 hours at room temperature, poured onto ice and extracted with ether. The organic phase is washed, dried and evaporated in vacuum. The title compound (Compound 25) is obtained as an oil by chromatography over silica gel (with toluene/ethylacetate 3/1).

Compounds 26, 27 and 28 are obtained in a manner analogous to that described in Example 3.

EXAMPLE 4

N-Methyl-N-(1-naphthylmethyl)-5-ethyl-5-hepten-3-yn-amine

To a solution of 630 mg N-methyl-N-(1-naphthylmethyl)-5-ethyl-5-hydroxy-3-heptyn-amine in $CH_2Cl_2$ are added, dropwise, at −20° 0.5 ml triethylamine and thereafter 0.21 ml mesylchloride, dissolved in $CH_2Cl_2$. The mixture is stirred for 3 hours at room temperature, washed several times with water, the organic phase is dried and evaporated. The residue is chromatographed over silica gel (with toluene/ethylacetate 4/1) to give the title compound (Compound 29) as an oil.

INTERMEDIATES

A 5,5-Dimethyl-3-hexyn-1-ol

To a solution of 3.1 g 3,3-dimethyl-1-butyne in abs. THF are added dropwise at −20°, 28.3 ml a 1.6M solution of n-butyllithium in hexane. After 1 hour at −50° are added hexamethylphosphoric acid triamide and thereafter 40 ml of a 1.4M solution of ethylene oxide in ether. The mixture is stirred overnight, and then mixed with water. The aqueous phase is extracted with ether, the organic phases are dried and evaporated (at normal atmospheric pressure). The residue is distilled under water jet vacuum and the title compound obtained as an oil at 70°/16 Torr.

The following intermediates of formula IV are obtained in a manner analogous to that described in Example A.

| | $R_5$ | A | Characterisation | for Cpd. |
|---|---|---|---|---|
| B | —C(CH₃)=CH₂ | OH | Oil(bp. 84°/16 Torr) | 2 |
| C | —C(CH₃)(C₂H₅)CH₃ | OH | Oil(bp. 75–80°/18 Torr) | 4 |
| D | —C(CH₃)₂-phenyl | OH | Oil | 5 |
| E | phenyl | OH | Oil(bp. 77–89°/0.1 Torr) | 11 |
| F | —C(CH₃)(OC₂H₅)CH₃ | OH | Oil(bp. 110°/14 Torr) | 12 |
| G | —C(CH₃)₂-C₆H₄-F | OH | Oil(bp. 85–88°/0.1 Torr) | 18 |
| H | cyclohexyl (H) | OH | Oil | 21 |

I 3-(4-Fluorophenyl)-3-methyl-1-butyne (a) 3-(4-Fluorophenyl)-3-methyl-2-butanone To a solution of 5.84 g 2-(4-fluorophenyl)-2-methylpropionitrile in abs. diethylether are added dropwise at −30° and under inert gas, 22 ml of a 1.6M solution of methyllithium in diethylether. The cooling bath is then taken away and the mixture stirred for 3 hours at room temperature. The reaction mixture is poured onto ice, the organic phase stirred overnight with 6N HCl, washed after separation of the acid phase, dried and evaporated in vacuum. The thus obtained oily residue is reacted further without purification.

NMR 6.8–7.4 (m, 4H); 1.94 (s, 3H); 1.5 (s, 6H). (b) 3-(4-Fluorophenyl)-3-methyl-1-butyne.

4.8 g 3-(4-Fluorophenyl)-3-methyl-2-butanone are stirred for 1 hour at room temperature with 11 g phosphorous pentachloride in 60 ml CCl₄. The mixture is poured onto ice, the organic phase separated, washed, dried and evaporated in vacuum. The residue is dissolved in dimethylsulfoxide (DMSO), added dropwise to a mixture of 3 g pulverised KOH and 50 ml DMSO, and heated overnight at 120°. The mixture is then poured onto ice, extracted with pentane the organic phase washed, dried and evaporated. bp. 72°–75°/14 Torr.

K N-Methyl-(2H-1-benzopyran-4-yl)methanamine

To 30 ml of a 33% solution of methanamine in ethanol are added dropwise 3 g 4-chloromethyl-2H-1-benzopyrane. The mixture is stirred overnight at room temperature, evaporated in vacuum, the residue dissolved in 1N HCl and extracted with CH₂Cl₂. The acid aqueous phase is rendered alkaline and extracted with CH₂Cl₂. The organic phase is washed, dried and evaporated, to give the title compound.

| NMR SPECTRA (CDCl₃—TMS) |
|---|
| A 3.68 (qua, J = 6.5 Hz, 2H); 2.22 (t, J = 6.5 Hz, 2H); 1.85 (t, J = 6.5 Hz, OH); 1.2 (s,9H). |
| B 5.1–5.3 (m, 2H); 3.6–3.9 (m, 2H); 2.56 (t, J = 6.5 Hz, 2H); 1.85 (pst, 3H); 1.8 (br, OH). |
| C 3.5–3.8 (br, 2H); 2.44 (t, J = 6 Hz, 2H); 1.8 (br, OH); 1.4 (pseudoqua, 2H); 1.15 (s, 6H); 0.95 (t, J = 7 Hz, 3H). |
| D 7.2–7.65 (m, 5H); 3.75 (qua, J = 6 Hz, 2H); 2.54 (t, J = 6 Hz, 2H); 1.84 (t, J = 6 Hz, OH); 1.58 (s, 6H). |
| E 7.2–7.5 (m,. 5H); 3.82 (qua, J = 6.5 Hz, 2H); 2.78 (t, J = 6.5 Hz, 2H); 1.95 (t, J = 6.5 Hz, OH). |
| F 3.45–3.85 (m, 4H); 2.5 (t, J = 7 Hz, 2H); 2.0 (t, J = 6.5 Hz, 1.25 (s, 6H); 1.2 (t, J = 7 Hz, 3H). |
| G 8.2–8.4 (m, 1H); 7.7–7.95 (m, 2H); 7.3–7.6 (m, 6H); 6.96 (t, J = 9 Hz, 2H); 3.9 (s, 2H); 2.4–2.9 (m, 4H); 2.28 (s, 3H); 1.52 (s, 6H). |
| H 3.7 (t, J = 6 Hz, 2H); 3.2 (br, OH); 2.4 (t, J = 6 Hz, 2H + m, 1H); 1.2 (m, 10H). |
| J 7.3–7.6 (m, 2H); 6.9–7.1 (pst, J = 9 Hz, 2H); 2.36 (s, 1H); 1.60 (s, 6H). |
| K 6.7–7.4 (m, 4H); 5.8 (pst, 1H); 4.8 (m, 2H); 3.6 (br, 2H); 2.5 (s, 3H); 2.4 (br, NH). |

I claim:

1. A compound of the formula:

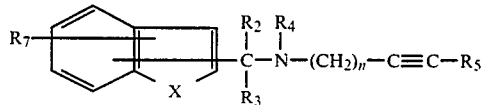

wherein

X is O, S, OCH₂ or SCH₂, n is 2 or 3, $R_2$ is H or $C_{1-4}$alkyl, either $R_3$ and $R_4$, independently, are H or $C_{1-4}$alkyl, or $R_3$ and $R_4$ together are $(CH_2)_u$, in which u is a number of 3 to 5, and $R_5$ is H, $C_{3-6}$alkenyl or is a group selected from $C_{1-12}$alkyl, tri($C_{1-12}$alkyl)silyl, di($C_{1-12}$alkyl)phenylsilyl, phenyl, phenyl($C_{1-12}$alkyl) and $C_{3-6}$cycloalkyl, in which the alkyl, phenyl and cycloalkyl groups or moieties are unsubstituted or substituted by OH, $C_{1-4}$alkyl, $C_{1-4}$alkoxy, phenyl or halogen, $R_7$ is H, halogen, $CF_3$, $C_{1-4}$alkyl or $C_{1-4}$alkoxy, in free base or acid addition salt form.

2. Compounds of claim 1, wherein x is O or S $R_7$ is H, halogen or $C_{1-4}$alkyl $R_2$ is H or $C_{1-4}$alkyl either $R_3$ is H and $R_4$ is $C_{1-4}$alkyl or $R_3$ together with $R_4$ is —$(CH_2)_4$- and $R_5$ is H, $C_{1-8}$alkyl, $C_{3-6}$cycloalkyl, $C_{3-5}$alkenyl, $C_{1-4}$alkoxy-$C_{1-5}$alkyl, phenyl-$C_{1-5}$alkyl, halogenphenyl-$C_{1-5}$alkyl, hydroxy-$C_{1-5}$alkyl, tri($C_{1-5}$alkyl)silyl, di($C_{1-5}$alkyl)phenylsilyl.

3. Compounds according to claim 2, wherein $R_2$ and $R_3$ are H
$R_4$ is $C_{1-4}$alkyl
$R_5$ is H, $C_{3-6}$cycloalkyl or a tertiary group selected from $C_{4-5}$alkyl, $C_{1-4}$alkoxy-$C_{3-5}$alkyl, halogenphenyl-$C_{3-5}$alkyl, phenyl-$C_{3-5}$alkyl or hydroxy-$C_{3-5}$alkyl which group is tied by its tert. carbon atom to the homopropargyl group.

4. A compound of claim 1 in which $R_3$ and $R_4$ are independently H or $C_{1-4}$alkyl.

5. The compound of claim 1 of the formula:

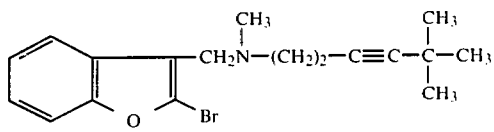

in free base or acid addition salt form.

6. The compound of claim 1 of the formula:

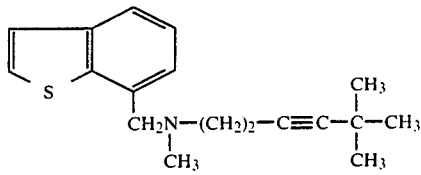

in free base or acid addition salt form.

7. The compound of claim 1 of the formula:

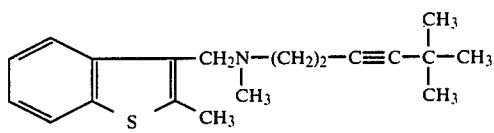

in free base or acid addition salt form.

8. The compound of the formula:

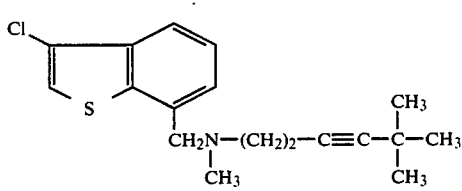

in free base or acid addition salt form.

9. The compound of the formula:

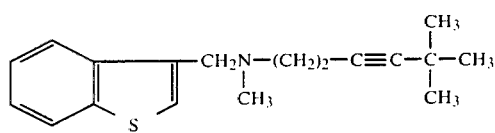

in free base or acid addition salt form.

10. The compound of the formula:

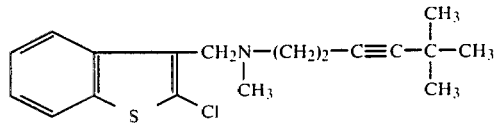

in free base or acid addition salt form.

11. The compound of the formula:

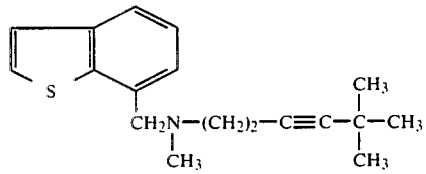

in free base or acid addition salt form.

12. An agricultural composition for combatting phytopathogenic fungi comprising an agriculturally acceptable diluent and a fungicidally effective amount of a compound of claim 1, in free form or in agriculturally acceptable acid addition salt form.

13. A method of combatting phytopathogenic fungi which comprises applying to the fungi or the locus thereof, a fungicidally effective amount of a compound according to claim 1 in free form or in agriculturally acceptable acid addition salt form.

14. A method of combatting phytopathogenic fungi which comprises applying to the fungi or the locus thereof, a fungicidally effective amount of a compound according to claim 2, in free form or in agriculturally acceptable acid addition salt form.

15. A method of combatting phytopathogenic fungi which comprises applying to the fungi or the locus thereof, a fungicidally effective amount of a compound according to claim 3, in free form or in agriculturally acceptable acid addition salt form.

* * * * *